United States Patent
Watanabe et al.

(10) Patent No.: US 10,556,038 B2
(45) Date of Patent: Feb. 11, 2020

(54) DERMATOLOGICAL ADHESIVE AGENT, PATCH MATERIAL, AND METHOD FOR PRODUCING DERMATOLOGICAL ADHESIVE AGENT

(71) Applicant: ALCARE CO., LTD., Tokyo (JP)

(72) Inventors: Ryota Watanabe, Tokyo (JP); Wataru Okuyama, Tokyo (JP)

(73) Assignee: ALCARE CO., LTD, Tokyo (JP)

( * ) Notice: Subject to any disclaimer, the term of this patent is extended or adjusted under 35 U.S.C. 154(b) by 71 days.

(21) Appl. No.: 15/116,686

(22) PCT Filed: Feb. 4, 2015

(86) PCT No.: PCT/JP2015/053123
§ 371 (c)(1),
(2) Date: Aug. 4, 2016

(87) PCT Pub. No.: WO2015/119160
PCT Pub. Date: Aug. 13, 2015

(65) Prior Publication Data
US 2016/0346422 A1 Dec. 1, 2016

(30) Foreign Application Priority Data

Feb. 5, 2014 (JP) .................. 2014-020562

(51) Int. Cl.
*A61L 15/42* (2006.01)
*A61L 24/00* (2006.01)
*A61L 15/58* (2006.01)
*A61L 24/04* (2006.01)

(52) U.S. Cl.
CPC .......... *A61L 15/585* (2013.01); *A61L 15/425* (2013.01); *A61L 24/0036* (2013.01); *A61L 24/043* (2013.01)

(58) Field of Classification Search
None
See application file for complete search history.

(56) References Cited

U.S. PATENT DOCUMENTS

| | | | | |
|---|---|---|---|---|
| 4,393,080 A | * | 7/1983 | Pawelchak | A61L 24/043 428/355 BL |
| 5,492,943 A | * | 2/1996 | Stempel | A61L 24/043 523/111 |
| 5,900,473 A | * | 5/1999 | Acevedo | C08G 18/4202 522/104 |
| 7,713,606 B2 | * | 5/2010 | Kasahara | B65H 37/007 428/195.1 |
| 2007/0213459 A1 | | 9/2007 | Tamai et al. | |
| 2008/0217382 A1 | * | 9/2008 | Kim | B23K 35/22 228/177 |
| 2013/0096208 A1 | * | 4/2013 | Koehler | A61K 8/062 514/784 |

FOREIGN PATENT DOCUMENTS

| | | |
|---|---|---|
| CN | 1914272 A | 2/2007 |
| JP | 6-108018 A | 4/1994 |
| JP | 2005-261453 A | 9/2005 |
| JP | 2006-263042 A | 10/2006 |
| JP | 2006-288690 A | 10/2006 |
| JP | 2008-56805 A | 3/2008 |
| JP | 2011-182847 A | 9/2011 |
| JP | 2014-114331 A | 6/2014 |
| WO | WO2011098505 * | 8/2011 |
| WO | WO2011109672 * | 9/2011 |
| WO | 2014-080954 A1 | 5/2014 |

OTHER PUBLICATIONS

Illinois Department of Public Health, Fiberglass Environmental Health Fact Sheet, http://www.idph.state.il.us/envhealth/factsheets/fiberglass.htm (Year: 2011).*

* cited by examiner

*Primary Examiner* — Jennifer A Berrios
(74) *Attorney, Agent, or Firm* — W&C IP

(57) ABSTRACT

Provided are a dermal adhesive composed of a radiation-curable resin and capable of reducing stuffiness that causes rash or itch, a patch including the dermal adhesive, and a method for producing the dermal adhesive. Also provided is a porous membranous dermal adhesive formed through irradiation of a radiation-curable resin with radiation rays. Further provided is a patch including a base sheet and the dermal adhesive disposed on the base sheet. Still further provided is a method for producing a porous membranous dermal adhesive, the method including applying a dermal adhesive composition containing a radiation-curable resin to an adherend so as to form a porous membranous dermal adhesive, and irradiating the dermal adhesive composition with radiation rays.

12 Claims, 3 Drawing Sheets

[Fig.1]
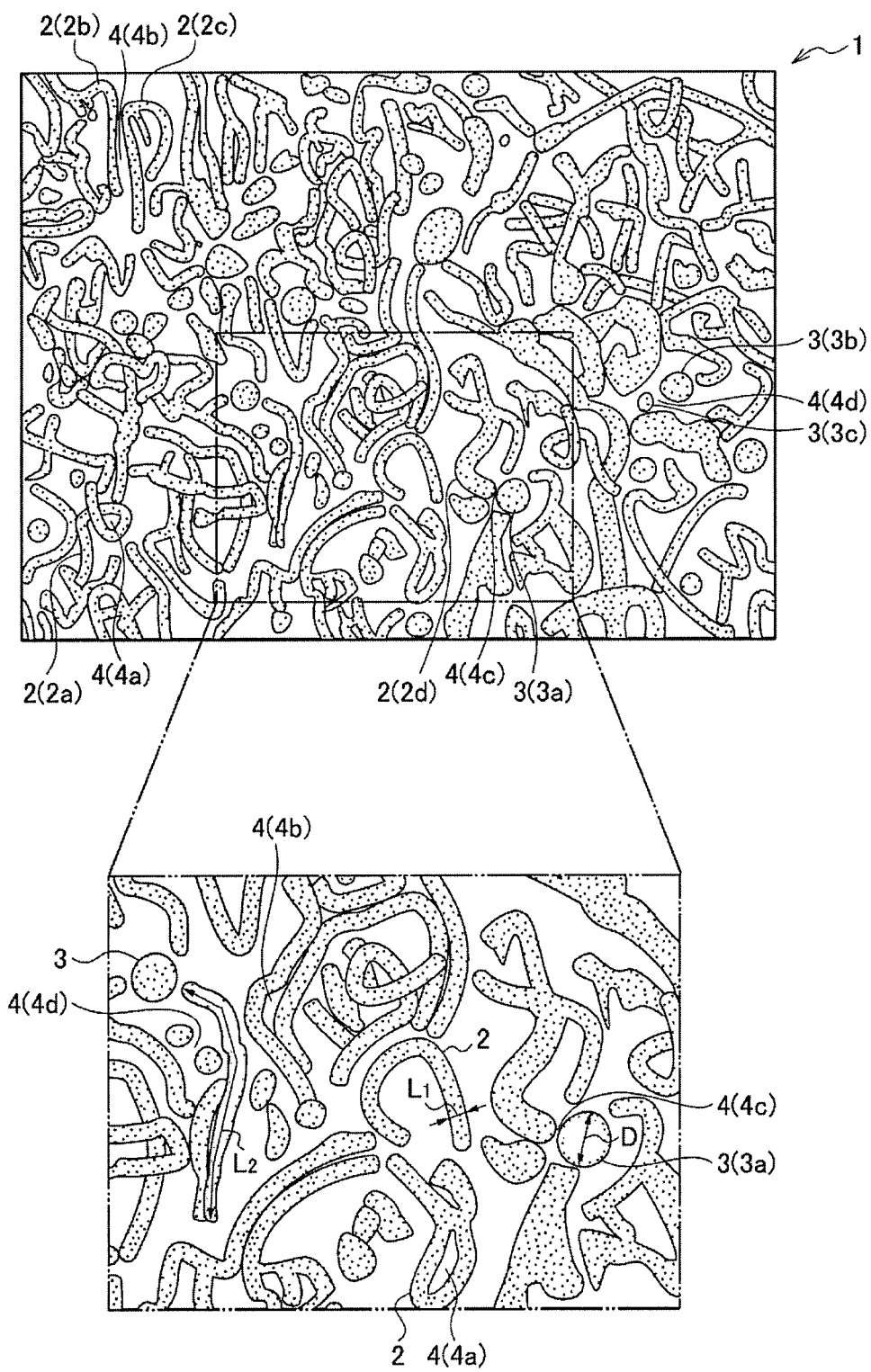

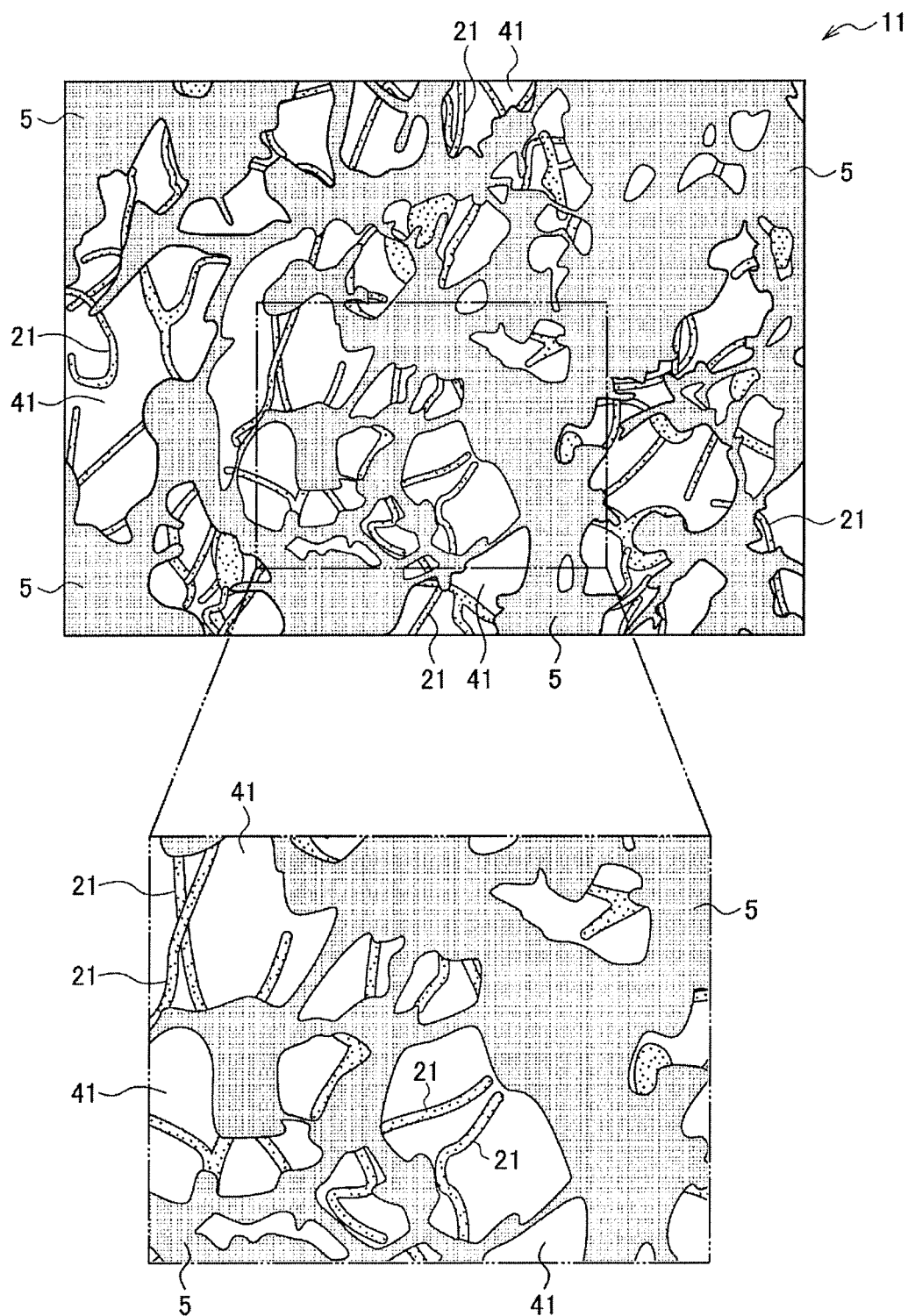
[Fig.2]

[Fig.3]
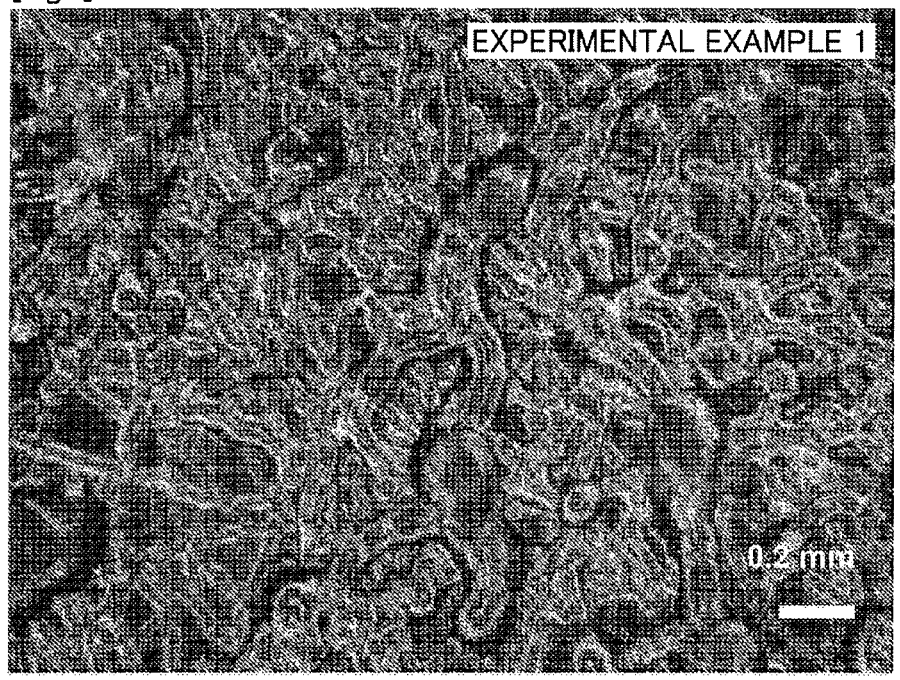
[Fig.4]
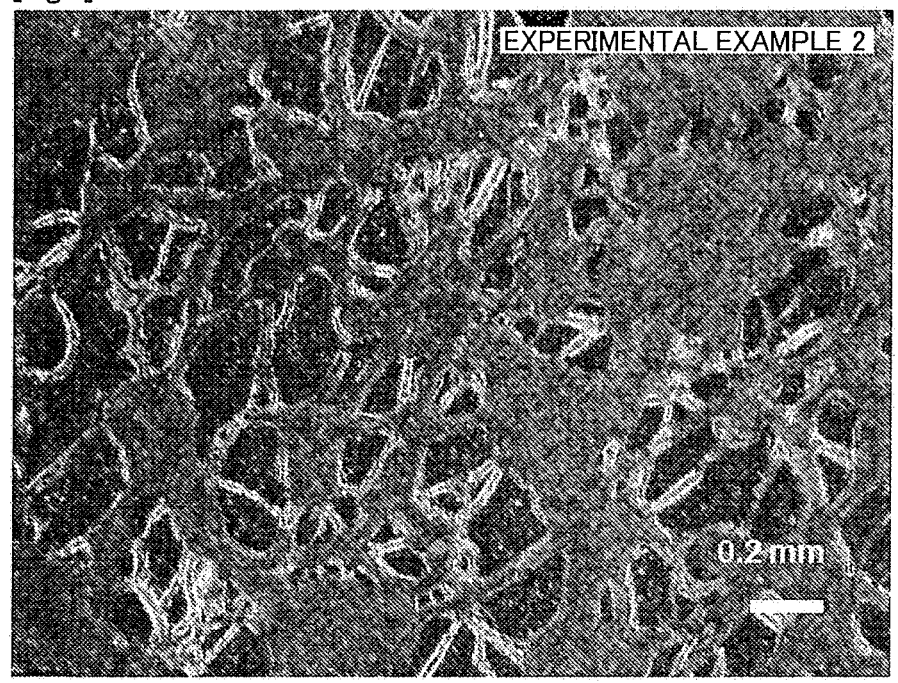

DERMATOLOGICAL ADHESIVE AGENT, PATCH MATERIAL, AND METHOD FOR PRODUCING DERMATOLOGICAL ADHESIVE AGENT

TECHNICAL FIELD

The present technique relates to a dermal adhesive, a patch comprising the dermal adhesive, and a method for producing the dermal adhesive.

BACKGROUND ART

Patches have been used for fixation of medical materials and devices (e.g., gauzes, bandages, plasters, catheters, and ostomy appliances) to the skin, and for protection and treatment of the skin, wounds, and peripheral portions of stomas.

A traditional dermal adhesive used in a patch contains an adhesive resin component and a component having a predetermined function.

For example, PTL 1 discloses an adhesive composition for a dermal patch, the composition containing an elastomer, a hygroscopic compound, a ceramide, and an emulsifier in a predetermined proportion.

CITATION LIST

Patent Literature

PTL 1: Japanese Unexamined Patent Application Publication No. 2006-263042

SUMMARY OF INVENTION

The present invention provides a porous membranous dermal adhesive formed through irradiation of a radiation-curable resin with radiation rays.

The present invention also provides a patch comprising a base sheet and the porous membranous dermal adhesive disposed on the base sheet.

The present invention also provides a method for producing a porous membranous dermal adhesive, the method comprising:

A) applying a dermal adhesive composition containing a radiation-curable resin to an adherend so as to form a porous membranous dermal adhesive, and B) irradiating the dermal adhesive composition with radiation rays.

BRIEF DESCRIPTION OF DRAWINGS

FIG. 1 is a schematic partial plan view of a dermal adhesive according to an embodiment of the present technique and is a partial enlarged view of the partial plan view.

FIG. 2 is a schematic partial plan view of a dermal adhesive according to another embodiment of the present technique, the dermal adhesive including a fibrous or particulate resin having a collapsed structure, and is a partial enlarged view of the partial plan view.

FIG. 3 is a photograph (substitute for drawing) of a dermal adhesive of Experimental Example 1.

FIG. 4 is a photograph (substitute for drawing) of a dermal adhesive of Experimental Example 2.

DESCRIPTION OF EMBODIMENTS

The present inventors have conducted extensive studies on a dermal adhesive containing a radiation-curable resin as a main component, in view of, for example, safety, environmental load, and productivity, among various adhesives.

In order to enhance the productivity of a patch comprising an adhesive, it is important to decrease the viscosity of the adhesive during coating of the adhesive and thus to increase the coating speed and improve the handling of the adhesive. The radiation-curable resin, which is cured through irradiation with radiation rays, requires compatibility between high productivity and reliable irradiation for preventing generation of an uncured portion.

A dermal adhesive or patch, which may be attached to the skin for a long period of time, requires a reduction in stuffiness that may cause rash or itch. For a reduction of stuffiness, the adhesive layer of the patch may be provided with breathability or a water-absorbing component may be compounded into the adhesive layer.

The present inventors have found that if an adherend surface is coated with an adhesive having a low viscosity to form a predetermined porous pattern for providing the resultant adhesive layer with breathability, the adhesive flows, which clogs the pores.

The present technique provides a dermal adhesive comprising a radiation-curable resin as a resin component for forming the adhesive. The dermal adhesive reduces stuffiness that may cause rash or itch, and is produced at high productivity. The present technique also provides a patch comprising the dermal adhesive, and a method for producing the dermal adhesive.

According to the present technique, the dermal adhesive can reduce stuffiness that causes rash or itch, and can be produced at high productivity. The present technique provides a patch comprising the dermal adhesive, and a method for producing the dermal adhesive.

Preferred embodiments of the present technique will now be described. The following embodiments are mere typical embodiments of the present technique and should not be construed to limit the present technique.

<Dermal Adhesive>

The dermal adhesive according to an embodiment of the present technique is formed through irradiation of a radiation-curable resin with radiation rays. The dermal adhesive is in the form of a porous membrane.

The dermal adhesive can be formed with a dermal adhesive composition at least containing a radiation-curable resin. The dermal adhesive may be formed only of the radiation-curable resin, but is preferably formed of a dermal adhesive composition containing the radiation-curable resin and any additional component. Thus, the porous membranous dermal adhesive of the present disclosure, which is formed through irradiation of a radiation-curable resin with radiation rays, also includes a porous membranous dermal adhesive formed through irradiation of a dermal adhesive composition containing the radiation-curable resin with radiation rays.

In the present disclosure, the term "porous membranous" refers to an adhesive in the form of a porous membrane (layer). The term "porous" refers to a structure having regularly or randomly provided through and/or non-through holes. The dermal adhesive of the present embodiment preferably has a porous membranous structure having randomly provided holes, which can be readily formed. A plurality of membranes having such a structure may be laminated together.

The porous membrane composed of the adhesive may have, for example, a fibrous, particulate, dot, grid, network, stripe, or arabesque pattern, or any combination of these patterns. In particular, the dermal adhesive is preferably composed of randomly disposed fibrous and particulate adhesives. The pores may have a circular or polygonal shape, or a quadrangular shape, for example, substantially a trapezoidal or parallelogram shape. Lamination of the porous membranes having such a pattern along the thickness can readily provide voids between the membranes. Random disposition of fibrous resins along the thickness of the dermal adhesive readily forms voids in the dermal adhesive, which tends to result in high water absorbance and favorable texture of the dermal adhesive.

The porous membranous dermal adhesive may be in the form of a film or sheet that can retain its shape. If the porous membranous dermal adhesive cannot retain its shape, for example, film or sheet, the dermal adhesive may be disposed on abase sheet.

The porous membranous dermal adhesive is formed through irradiation of a radiation-curable resin with radiation rays. Thus, the dermal adhesive is in the form of a membrane prepared through curing of the radiation-curable resin.

The porous membranous dermal adhesive has a porosity of preferably 5 to 90%, more preferably 10 to 70%, still more preferably 15 to 50%, in view of compatibility between high breathability of the dermal adhesive and high adhesion of the dermal adhesive to the skin. In the present disclosure, the porosity is determined through analysis of an optical microscopic image of the surface of the dermal adhesive, as described below in Examples.

The lower limit of the porosity is preferably 5%, more preferably 10%, still more preferably 15%, in view of high breathability of the dermal adhesive. The upper limit of the porosity is preferably 80%, more preferably 60%, still more preferably 40%, in view of high adhesion of the dermal adhesive to the skin.

The dermal adhesive preferably has a porous membranous structure formed of fibrous resins containing the radiation-curable resin and having voids defined between the fibrous resins. This porous membranous structure leads to compatibility between high breathability of the dermal adhesive and favorable texture of the dermal adhesive to the skin. The fibrous resin, which is a component of the dermal adhesive, can be regarded as a fibrous adhesive.

The fibrous resin, which is a component of the porous membranous dermal adhesive, is composed of at least a radiation-curable resin. If the dermal adhesive is composed of a dermal adhesive composition containing the radiation-curable resin and any additional component, the fibrous resin may contain the radiation-curable resin and the additional component.

The porous membranous dermal adhesive is formed through combination of one or more fibrous resins and has voids defined between the fibrous resins (see FIG. 1 and FIG. 3 (a dermal adhesive prepared in Examples described below)). If the porous membranous dermal adhesive is composed of fibrous resins, the fibrous resins may be entangled and aggregated to define voids between the fibrous resins, to prepare the porous membranous dermal adhesive. If the porous membranous dermal adhesive is composed of a plurality of fibrous resins, the porous membranous dermal adhesive may have voids defined in one fibrous resin or voids defined between different fibrous resins. Preferably, the porous membranous dermal adhesive is formed through combination of a plurality of fibrous resins and has voids defined between the fibrous resins in view of production efficiency.

The porous membranous dermal adhesive, which is composed of a fibrous resin described above, may also include a particulate resin containing a radiation-curable resin (see FIG. 1 and FIG. 3 (a dermal adhesive prepared in Examples described below)). The dermal adhesive may contain a plurality of particulate resins. In this case, the dermal adhesive has voids defined between a plurality of (a large number of) particulate resins. The presence of these voids can provide favorable breathability of the dermal adhesive. The particulate resin, which is a component of the dermal adhesive, can be regarded as a particulate adhesive.

The dermal adhesive is preferably in the form of a porous membrane formed through combination of fibrous resins and/or particulate resins containing a radiation-curable resin and having voids defined between the fibrous resins and/or the particulate resins. As used herein, the term "between fibrous resins and/or particulate resins" includes "between a fibrous resin and another fibrous resin," "between a particulate resin and another particulate resin," and "between a fibrous resin and a particulate resin."

The structure of the dermal adhesive comprising fibrous resins and particulate resins will be morphologically described in detail with reference to FIG. 1.

FIG. 1 is a schematic partial plan view of the dermal adhesive 1 according to the present embodiment and is a partial enlarged view of the partial plan view. As illustrated in FIG. 1, the porous membranous dermal adhesive 1 comprises fibrous resins 2 and particulate resins 3 containing a radiation-curable resin and has voids 4.

As illustrated in FIG. 1, the dermal adhesive 1 has a void (4a) defined in a fibrous resin (2a) with the fibrous resin entangled (2a). The dermal adhesive 1 also has avoid (4b) between a plurality of fibrous resins; i.e., between a fibrous resin (2b) and another fibrous resin (2c). The dermal adhesive 1 also has a void (4c) between a particulate resin (3a) and a fibrous resin (2d). The dermal adhesive 1 also has a void (4d) between a particulate resin (3b) and another particulate resin (3c).

As described above, the dermal adhesive 1 has various types of voids 4 defined between fibrous resins 2 and/or between particulate resins 3. The dermal adhesive 1 has a porous membranous structure formed through combination of the fibrous resins 2 and/or particulate resins 3 and having the voids 4.

As illustrated in FIG. 1, the dermal adhesive 1 preferably includes fibrous resins 2 greater in number than particulate resins 3. If the number of fibrous resins 2 is greater than that of particulate resins 3 in the porous membranous dermal adhesive 1, the fibrous resins 2 can readily provide a dermal adhesive 1 with a non-woven fabric structure. The resultant dermal adhesive 1 exhibits an appropriate adhesion and a favorable texture to the skin.

Each fibrous resin may have any fiber diameter (also referred to as "fiber thickness," see $L_1$ in FIG. 1, for example). The fiber diameter is typically 1 to 1,000 µm, preferably 5 to 500 µm, more preferably 10 to 300 µm, still more preferably 15 to 100 µm. The presence of fibrous resins having a fiber diameter within the aforementioned range leads to formation of a dermal adhesive exhibiting a favorable texture and adhesion to the skin and high cohesiveness.

The upper limit of the fiber diameter is typically 1,000 µm, preferably 400 µm, more preferably 200 µm, still more preferably 80 µm, in view of a favorable texture and adhesion to the skin. The lower limit of the fiber diameter is typically 0.1 µm, preferably 15 µm, more preferably 20 µm, still more preferably 25 µm, in view of preparation of a dermal adhesive exhibiting high cohesiveness.

In the present disclosure, the fiber diameter of the fibrous resin is determined as described below in Examples. In specific, three measuring points are randomly selected in fibrous resins in an optical microscopic image of the surface of the dermal adhesive, and the fiber diameter (fiber thickness) is determined on the basis of the averaged diameters (thicknesses) of the three measuring points.

Each fibrous resin may have any length (also referred to as "fiber length," see $L_2$ in FIG. 1, for example). The fiber length is preferably 0.1 to 10 mm, more preferably 0.5 to 9 mm, still more preferably 1 to 7 mm. A fibrous resin having such a length is readily entangled to provide a void or voids in the entangled fibrous resin.

In the present disclosure, the fiber length is determined as described below in Examples. In detail, three fibrous resins are randomly selected in an optical microscopic image of the surface of the dermal adhesive, and the length of fibrous resins is determined on the basis of the averaged lengths of the three fibrous resins. The fiber length of a fibrous resin is approximated by the length of a broken line drawn along the fibrous resin (see $L_2$ in FIG. 1).

Each particulate resin may have any particle size (see D in FIG. 1). The particle size is typically 1 to 1,000 μm, preferably 5 to 500 μm, more preferably 10 to 300 μm, still more preferably 15 to 100 μm. The presence of particulate resins having a particle size within the aforementioned range leads to formation of a dermal adhesive exhibiting a favorable texture and adhesion to the skin and high cohesiveness. The particle size is determined as described below. Three measuring points are randomly selected in particulate resins in an optical microscopic image of the surface of the dermal adhesive, and the particle size is measured on the basis of the averaged sizes of the three points of particulate resins as in the aforementioned fiber diameter.

The porous membranous dermal adhesive including the aforementioned fibrous resins, particulate resins, and voids is preferably formed through a blowing process (more preferably melt blowing, still more preferably curtain spray coating). Such a process involves discharge of a dermal adhesive composition containing a radiation-curable resin in a fibrous and/or particulate form, and irradiation of the discharged dermal adhesive composition with radiation rays. This process can readily form the porous membranous dermal adhesive including the aforementioned fibrous resins, particulate resins, and voids.

In some cases, lamination of the dermal adhesive on a base sheet or transfer of the dermal adhesive from a transfer sheet to a base sheet may cause collapse of fibrous resins or particulate resins of the dermal adhesive of the dermal adhesive sheet. Alternatively, fibrous resins or particulate resins of the dermal adhesive of the dermal adhesive sheet may collapse because of the weight of the sheet itself or a product disposed on the sheet during storage of the sheet after production thereof.

FIG. 2 illustrates a dermal adhesive including a fibrous or particulate resin having a collapsed structure. As illustrated in FIG. 2, the dermal adhesive 11 includes fibrous resins 21, voids 41, and a continuous segment 5 formed through collapse of fibrous resins or particulate resins. The dermal adhesive 11 has a porous membranous structure even after collapse of fibrous resins or particulate resins. Although not illustrated in FIG. 2, the dermal adhesive 11 may include particulate resins.

The dermal adhesive exhibits a breathability (air permeability) of preferably 1.5 seconds or less, more preferably 1.3 seconds or less, still more preferably 1.0 second or less, the breathability (air permeability) being measured in accordance with method B (Gurley method) of JIS L1096 in the form of a dermal adhesive sheet prepared by disposition of the dermal adhesive on a base sheet. The dermal adhesive having such an air permeability exhibits high breathability and can readily reduce stuffiness that causes rash or itch.

The dermal adhesive has a water absorption of preferably 50 to 300%, more preferably 60 to 200%, still more preferably 70 to 150%. Such a preferred water absorption can be achieved by modification of the porous membranous structure of the dermal adhesive and incorporation of any of the below-described usable hydrophilic polymers into the dermal adhesive. The dermal adhesive having a water absorption within the aforementioned range can rapidly absorb moisture, such as sweat or exudate.

In the present disclosure, the water absorption is determined in accordance with JIS T9233 4.5.1 "measurement of a variation in mass." In detail, the water absorption is calculated from the following expression:

water absorption (%)={[(mass after immersion)−(mass before immersion)]/(mass before immersion)}×100

, where "mass after immersion" corresponds to the mass of the dermal adhesive after immersion of the adhesive in saline (0.9% aqueous NaCl solution) for 24 hours, and "mass before immersion" corresponds to the mass of the dermal adhesive before immersion of the adhesive in the saline.

The water absorption is measured in the form of a dermal adhesive sheet prepared by disposition of the dermal adhesive on a base sheet. If the base sheet is a water-unabsorbable sheet, such as a PET film, the water absorption of the dermal adhesive sheet is almost equal to that of the dermal adhesive.

The dermal adhesive may have any thickness. Preferably, the dermal adhesive, which is formed through irradiation of a radiation-curable resin with radiation rays, has such a thickness that the resin can be sufficiently cured through irradiation with the radiation rays. In view of this, the thickness of the dermal adhesive is preferably 5 to 500 μm, more preferably 10 to 300 μm, still more preferably 20 to 200 μm.

The lower limit of the thickness of the dermal adhesive is preferably 10 μm, more preferably 20 μm, still more preferably 30 μm, in view of an increase in adhesive force of the dermal adhesive and an increase in the amount of an additional component (e.g., a hydrophilic polymer described below) in the dermal adhesive.

The upper limit of the thickness of the dermal adhesive is preferably 300 μm, more preferably 250 μm, still more preferably 200 μm, in view of sufficient curing of the radiation-curable resin.

[Radiation-Curable Resin]

The radiation-curable resin used in the dermal adhesive of the present embodiment will now be described. In the present disclosure, the term "radiation-curable resin" refers to a resin composition that are curable (or cross-linkable) through irradiation with radiation rays and contains at least one of a polymer, oligomer, and monomer as a component.

The "radiation rays" used herein may be any type of radiation rays with energy that can cure or crosslink the radiation-curable resin through, for example, radical polymerization, cationic polymerization, or anionic polymerization. Examples of the radiation rays include electron beams, ultraviolet rays, infrared rays, laser beams, visible rays, ionizing radiations (e.g., X rays, α rays, β rays, and γ rays), microwaves, and radiofrequency waves.

The radiation-curable resin used in the present embodiment is preferably cured (or cross-linked) with one or more types selected from the group consisting of electron beams, visible rays, and ultraviolet rays.

The radiation-curable resin is preferably one or more types selected from the group consisting of electron beam-curable resins, visible ray-curable resins, and ultraviolet ray-curable resins. The radiation-curable resin is more preferably an ultraviolet ray-curable resin, still more preferably a hot-melt ultraviolet ray-curable resin.

The radiation-curable resin may be cured through any mechanism. The mechanism is preferably radical polymerization, cationic polymerization, or photodimerization, more preferably radical polymerization or photodimerization.

Examples of the radiation-curable resin include (meth)acrylate resins, silicone resins, urethane resins, silicone (meth)acrylate resins, urethane (meth)acrylate resins, and epoxy (meth)acrylate resins. These radiation-curable resins may be used alone or in combination. The radiation-curable resin may be a mixture containing two or more species of the aforementioned resins.

The radiation-curable resin is preferably one or more species selected from the group consisting of (meth)_acrylate resins, silicone (meth)acrylate resins, urethane (meth)acrylate resins, and epoxy (meth)acrylate resins. The radiation-curable resin is more preferably an ultraviolet ray-curable (meth)acrylate resin.

In the present disclosure, the term "(meth)acrylate" refers to both "acrylate" and "methacrylate."

The radiation-curable resin is preferably a homopolymer and/or copolymer having a structural unit (repeating unit) derived from a (meth)acrylate having an alkyl group having 1 to 20 carbon atoms (more preferably 2 to 10 carbon atoms, still more preferably four to eight carbon atoms) or a cycloalkyl group having four to eight carbon atoms. The alkyl group or the cycloalkyl group may have any substituent. Examples of the substituent include halo, hydroxy, aryl, alkoxy, phenoxy, epoxy, norbornyl, and adamantyl.

The radiation-curable resin having such a structural unit is more preferably a homopolymer and/or copolymer having a structural unit derived from butyl (meth)_acrylate and/or a structural unit derived from 2-ethylhexyl (meth)acrylate. The radiation-curable resin is still more preferably a homopolymer and/or copolymer having a structural unit derived from butyl acrylate and/or a structural unit derived from 2-ethylhexyl acrylate.

The homopolymer and/or copolymer having such a structural unit may be any of oligomers described below and having a lower molecular weight.

The radiation-curable resin has a mass average molecular weight Mw of preferably 1,000 to 250,000, more preferably 1,000 to 200,000. The radiation-curable resin having a mass average molecular weight Mw within the aforementioned range can prepare a dermal adhesive composition at high productivity. The composition can form a uniform pattern through coating. Curing of the composition through irradiation with radiation rays can provide an adhesive with a large mass average molecular weight and high cohesiveness. In the present disclosure, the mass average molecular weight Mw is determined by gel permeation chromatography (GPC) (calculated in terms of polystyrene).

The radiation-curable resin may be a commercially available product. Examples of the commercially available radiation-curable resin include "3000 series (trade name)" and "3100 series (trade name)" (manufactured by ThreeBond Holdings Co., Ltd.), "UNIDIC (trade name)" series and "TYFORCE (trade name)" series (manufactured by DIC Corporation), "YUPIMER (trade name)" series (manufactured by Mitsubishi Chemical Corporation), "HITALOID (trade name)" series (manufactured by Hitachi Chemical Co., Ltd.), "BEAMSET (trade name)" series (manufactured by Arakawa Chemical Industries, Ltd.), "acResin (trade name)" series (manufactured by BASF), and "UVA-2000 series (trade name)" (manufactured by TOAGOSEI CO., LTD.).

The radiation-curable resin may be in the form of a resin composition containing one or more polymerizable oligomers and/or monomers in addition to or in place of the aforementioned homopolymer and/or copolymer having a structural unit derived from the (meth)acrylate described above. Such a polymerizable oligomer and/or monomer is preferably polymerized through radical or cationic polymerization, more preferably through radical polymerization.

Examples of the radically polymerizable oligomer include (meth)acrylate oligomers, polyester (meth)acrylate oligomers, urethane (meth)acrylate oligomers, silicone (meth)acrylate oligomers, and epoxy (meth)acrylate oligomers.

Examples of the radically polymerizable monomer include monomers having a (meth)acryloyl group. The monomer may have any number of (meth)acryloyl groups. Example of the monomer include monofunctional (meth)acrylates having one (meth)acryloyl group, difunctional (meth)acrylates having two (meth)acryloyl groups, and multifunctional (meth)acrylates having three or more (meth)acryloyl groups.

Examples of the cationically polymerizable oligomer or monomer include oligomers or monomers having an epoxy ring, an oxetane ring, an oxolane ring, a dioxolane ring, a vinyl ether structure, and a functional group having such a structure.

Examples of the cationically polymerizable oligomer or monomer include limonene oxide compounds commercially available from TOMOE Engineering Co., Ltd., "EPO-LIGHT (trade name)" series (glycidyl ether compounds commercially available from KYOEISHA CHEMICAL Co., Ltd.), and "ARONE OXETANE (trade name)" (oxetane compounds commercially available from TOAGOSEI CO., LTD.).

The radiation-curable resin used in the present embodiment preferably contains one or more species selected from the group consisting of the aforementioned polymerizable (meth)acrylate oligomers, urethane (meth)acrylate oligomers, and silicone (meth)acrylate oligomers.

The oligomer may have any molecular weight. The number average molecular weight Mn of the oligomer is preferably less than 10,000 (e.g., 1,000 or more and less than 10,000) in view of easy application of the radiation-curable resin or the dermal adhesive composition containing the resin. A polymerizable oligomer having a number average molecular weight Mn of 10,000 or more may be used. In the present disclosure, the number average molecular weight Mn is determined by gel permeation chromatography (GPC) (calculated in terms of polystyrene).

The radiation-curable resin may further contain, for example, a polymerization initiator, an additive, and/or a solvent.

The resin may contain any polymerization initiator known in the field of radiation-curable resin. Examples of the polymerization initiator include acetophenone initiators, benzophenone compounds, α-ketoester compounds, and benzoin compounds.

Instead of the polymerization initiator contained in the radiation-curable resin, it is preferable that the polymerization initiator is bonded to the molecular chain of a polymer or oligomer component of the radiation-curable resin. The use of the radiation-curable resin having a polymerizationinitiator-bonded molecular chain eliminates the need for further addition of a polymerization initiator and therefore, can prepare a dermal adhesive exhibiting high safety.

Examples of the radiation-curable resin having a polymerization-initiator-bonded molecular chain include "UV-H (trade name)" series (manufactured by KSM Co., Ltd.) and "acResin (trade name)" series (manufactured by BASF).

The polymerization-initiator-bonded radiation-curable resin may further contain an additional polymerization initiator, or the bonded polymerization initiator may be replaced with another one.

Examples of the photodimerizable oligomer or polymer include oligomers or polymers having maleimido groups.

Examples of the photodimerizable oligomer or polymer include "UVA-2000 (trade name)" series (maleimide-terminated polyester and polyether resins commercially available from TOAGOSEI CO., LTD.).

The dermal adhesive composition contains the radiation-curable resin in an amount of preferably 30 to 100 mass %, more preferably 35 to 95 mass %, still more preferably 40 to 90 mass %, much more preferably 55 to 85 mass %.

A radiation-curable resin content within the aforementioned range leads to high cohesiveness of the dermal adhesive prepared through irradiation of the radiation-curable resin with radiation rays. Such a radiation-curable resin content facilitates formation of hydrocolloid containing the below-described hydrophilic polymer dispersed in the radiation-curable resin.

As described above, the dermal adhesive of the present embodiment is composed of the dermal adhesive composition containing at least the radiation-curable resin.

The dermal adhesive composition, which contains the radiation-curable resin, may contain an additive in such an amount that the additive does not impair the advantageous effects of the present technique. Examples of the additive include hydrophilic polymers, reactive diluents that react with the radiation-curable resins, softeners (plasticizers), tackifiers, fillers, pH adjusters, and pharmaceutically active ingredients.

[Hydrophilic Polymer]

The dermal adhesive of the present embodiment preferably contains a hydrophilic polymer. More preferably, the hydrophilic polymer is dispersed in the radiation-curable resin. The dermal adhesive containing the hydrophilic polymer can be prepared from the dermal adhesive composition containing the radiation-curable resin and the hydrophilic polymer.

Incorporation of the hydrophilic polymer into the dermal adhesive facilitates absorption of moisture (e.g., sweat or exudate) during application of the dermal adhesive to the skin, resulting in relief of itch or rash caused by stuffiness. From this viewpoint, the dermal adhesive composition contains the hydrophilic polymer in an amount of preferably 1 to 30 mass %, more preferably 5 to 25 mass %, still more preferably 5 to 20 mass %. A hydrophilic polymer content within the aforementioned range contributes to relief of skin irritation caused by, for example, skin maceration, and achieves long-term application of the dermal adhesive to the skin.

The hydrophilic polymer used in the present embodiment may be any of natural, semisynthetic, and synthetic hydrophilic polymers. As used herein, the term "semisynthesis," which is also called "partial chemical synthesis," refers to a chemical synthesis involving the use of a compound isolated from a natural source, such as a plant material, a microorganism, or a cell culture, as a starting material.

Specific examples of the natural hydrophilic polymer include plant-derived polymers, such as gum Arabic, tragacanth gum, galactan, guar gum, carob gum, karaya gum, carrageenan, pectin, agar, and starch (e.g., rice starch, cornstarch, potato starch, and wheat starch); microorganism-derived polymers, such as xanthan gum, dextrin, dextran, succinoglucan, mannan, locust bean gum, and pullulan; and animal-derived polymers, such as casein, albumin, and gelatin.

Specific examples of the semisynthetic hydrophilic polymer compound include starch polymers (e.g., carboxymethyl starch and methylhydroxypropyl starch); cellulose polymers (e.g., methyl cellulose, ethyl cellulose, methylhydroxypropyl cellulose, hydroxyethyl cellulose, cellulose sodium sulfate, hydroxypropyl cellulose, carboxymethyl cellulose, and sodium carboxymethyl cellulose); and polyalginates, e.g., poly(sodium alginate) and poly(propylene glycol alginate).

Specific examples of the synthetic hydrophilic polymer compound include vinyl polymers (e.g., poly(vinyl alcohol), poly(vinyl methyl ether), polyvinylpyrrolidone, and carboxyvinyl polymers); acrylic polymers (e.g., poly(sodium acrylate) and polyacrylamide); and polyethyleneimine.

The hydrophilic polymers may be used alone or in combination.

Among the aforementioned hydrophilic polymers, preferred are one or more species selected from the group consisting of sodium carboxymethyl cellulose, pectin, karaya gum, mannan, locust bean gum, and gelatin, and more preferred are one or more species selected from the group consisting of sodium carboxymethyl cellulose, mannan, and locust bean gum. The use of such a hydrophilic polymer facilitates formation of hydrocolloid.

[Reactive Diluent]

The reactive diluent is a liquid that can react with the radiation-curable resin and reduces the viscosity or resin content of the dermal adhesive composition.

Incorporation of the reactive diluent into the dermal adhesive composition facilitates coating process of the composition, for example. Since the reactive diluent reacts with the radiation-curable resin to form cross-links through irradiation of the composition with radiation rays, the resultant dermal adhesive exhibits high cohesiveness and causes less bleeding.

The reactive diluent is preferably a compound having one to three (meth)acryloyl groups per molecule. As used herein, the term "(meth)acryloyl group" refers to both "acryloyl group" ($H_2C=CH-C(=O)-$) and "methacryloyl group" ($H_2C=C(CH_3)-C(=O)-$).

The compound having a (meth)acryloyl group may have any molecular weight. The molecular weight is preferably 1,000 or less, more preferably 800 or less, still more preferably 600 or less.

The compound having a (meth)acryloyl group, which is used as the reactive diluent, is a (meth)acrylate compound or a (meth)acrylamide compound, for example. As used herein, the "(meth)acrylate compound" refers to a (meth)acrylate ester compound having a linear or branched alkyl or cycloalkyl group that may have any substituent. The "(meth)acrylamide compound" refers to an amide compound having a (meth)acryloyl group wherein the amino group of the (meth)acrylamide may have any substituent. The term "(meth)acryl" refers to both "acryl" and "methacryl."

The "(meth)acrylate compound" or "(meth)acrylamide compound" may have any substituent. Examples of the substituent include hydroxyl, alkoxy, and phenoxy.

The reactive diluent may be at least one of one or more monomers selected from the compounds having a (meth)acryloyl group and oligomers composed of such monomers.

The reactive diluent is preferably at least one species selected from the group consisting of acryloylmorpholine, hydroxyethylacrylamide, phenoxyethyl acrylate, 1,3-dioxolane acrylate, isobornyl acrylate, poly(ethylene glycol) diacrylate, propylene oxide (PO)-modified trimethylolpropane triacrylate, and methoxypoly(ethylene glycol) acrylate.

More preferred are one or more species selected from the group consisting of acryloylmorpholine, poly(ethylene glycol) diacrylate, and PO-modified trimethylolpropane triacrylate.

Examples of the (meth)acrylate compound used as the reactive diluent include monofunctional (meth)acrylate compounds having one (meth)acryloyl group, difunctional (meth)acrylate compounds having two (meth)acryloyl groups, and multifunctional (meth)acrylate compounds having three or more (meth)acryloyl groups.

Examples of the monofunctional (meth)acrylate compound include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, isooctyl (meth)acrylate, 2-ethylhexyl (meth)acrylate, isodecyl (meth)acrylate, tridecyl (meth)acrylate, isoamyl (meth)acrylate, stearyl (meth)acrylate, lauryl (meth)acrylate, cyclohexyl (meth)acrylate, isobornyl (meth) acrylate, 2-hydroxyethyl (meth)acrylate, 2-hydroxypropyl (meth) acrylate, 2-hydroxybutyl (meth) acrylate, ethoxydiethylene glycol (meth) acrylate, methoxydiethylene glycol (meth) acrylate, methoxypoly(ethylene glycol) (meth)acrylate, phenoxyethyl (meth)acrylate, 2-hydroxy-3-phenoxypropyl (meth) acrylate, and cyclohexanespiro-2-(1,3-dioxolan-4-yl) methyl acrylate.

Examples of the difunctional (meth)acrylate compound include ethylene glycol di(meth)acrylate, diethylene glycol di(meth)acrylate, triethylene glycol di(meth)acrylate, tetraethylene glycol di(meth)acrylate, poly(ethylene glycol) di(meth)acrylate, dipropylene glycol dimethacrylate, tripropylene glycol di(meth)acrylate, 1,3-butylene glycol di(meth) acrylate, 1,4-butanediol di(meth)acrylate, 1,6-hexanediol di(meth)acrylate, and 1,9-nonanediol di(meth)acrylate.

Examples of the multifunctional (meth)acrylate compound include trimethylolpropane tri(meth)acrylate, alkylene oxide-modified trimethylolpropane tri(meth)acrylate, pentaerythritol tri(meth)acrylate, pentaerythritol tetra(meth)acrylate, ditrimethylolpropane tetra(meth)acrylate, dipentaerythritol penta(meth)acrylate, and dipentaerythritol hexa (meth)acrylate.

The "alkylene oxide-modified" of the aforementioned "alkylene oxide-modified trimethylolpropane tri(meth)acrylate" is "ethylene oxide (EO)-modified" or "propylene oxide (PO)-modified," for example.

The (meth)acrylate compounds used as the reactive diluent are preferably (meth)acrylates having a quaternary carbon atom with symmetricity at the carbon atom, such as (meth)acrylates having a trimethylolpropane skeleton. Examples of the (meth)acrylate having a trimethylolpropane skeleton include trimethylolpropane tri(meth)acrylate, ditrimethylolpropane tetra(meth)acrylate, and alkylene oxide-modified trimethylolpropane tri(meth)acrylate.

The reactive diluent has a viscosity at 25° C. of preferably 1,000 mPa·s or less, more preferably 500 mPa·s or less. The lower limit of the viscosity is preferably 1 mPa·s.

The reactive diluent having a viscosity at 25° C. within the above range is readily mixed with the radiation-curable resin and facilitates a coating process, for example. In the present specification, the viscosity at 25° C. (steady flow viscosity) of the reactive diluent is measured in accordance with JIS Z8803 with a single-cylinder rotary viscometer at 25° C.

The dermal adhesive composition may contain the reactive diluent in any amount. The reactive diluent content of the dermal adhesive composition is preferably 1 to 30 mass %. In order to effectively reduce the viscosity of the dermal adhesive composition and to increase the adhesive force of the dermal adhesive, the reactive diluent content of the dermal adhesive composition is preferably 1 to 20 mass %, more preferably 2 to 15 mass %, still more preferably 2 to 8 mass %.

A reactive diluent content within the above range leads to a reduction in viscosity of the dermal adhesive composition, an improvement in production efficiency, and ease of a coating process, for example. The resultant dermal adhesive composition readily provides a dermal adhesive that exhibits high cohesiveness and causes less bleeding. The dermal adhesive composition can reduce the cumulative amount of light required for curing, and thus contributes to an improvement in productivity and maintenance of the pattern of the coated adhesive.

[Functional Group-free Acrylic Polymer]

The dermal adhesive composition preferably contains a functional group-free acrylic polymer in combination with the reactive diluent.

The "acrylic polymer" of the functional group-free acrylic polymer refers to a polyacrylate or a polymethacrylate; i.e., a homopolymer or copolymer containing a main structural unit derived from an acrylate and/or methacrylate (structural unit content: 50 mol % or more). The amount (mol %) of the structural unit derived from an acrylate and/or methacrylate in the acrylic polymer is determined with a nuclear magnetic resonance (NMR) analyzer.

As used herein, the "functional group-free acrylic polymer" refers to an acrylic polymer having substantially no functional group other than an acryloyl group. Examples of the functional group other than an acryloyl group include OH, COOH, an epoxy group, and an alkoxysilyl group.

The functional group-free acrylic polymer has a mass average molecular weight (Mw) of preferably 1,000 to 9000, more preferably 1,500 to 8,000, still more preferably 2,000 to 6,000, in view of an effective reduction in viscosity of the dermal adhesive composition and efficient production of an adhesive having high cohesiveness. The mass average molecular weight Mw is determined by gel permeation chromatography (GPC) (calculated in terms of polystyrene).

The functional group-free acrylic polymer is preferably in the form of liquid at ambient temperature (20 to 30° C.) in view of an effective reduction in viscosity of the dermal adhesive composition. The functional group-free acrylic polymer in the form of liquid at ambient temperature has a solid content of preferably 90% or more, more preferably 95% or more, still more preferably 98% or more.

The functional group-free acrylic polymer has a viscosity at 25° C. of preferably 300 to 10,000 mPa·s, more preferably 400 to 6,000 mPa·s, still more preferably 500 to 5,000 mPa·s. In the present disclosure, the viscosity at 25° C. (steady flow viscosity) of the functional group-free acrylic polymer is measured in accordance with JIS Z8803 with a single-cylinder rotary viscometer at 25° C.

The functional group-free acrylic polymer has a glass transition point (Tg) of preferably −100 to −20° C., more preferably −90 to −40° C., still more preferably −80 to −60° C., in view of an effective reduction in viscosity of the dermal adhesive composition. The glass transition point Tg is determined with a differential scanning calorimeter (DSC).

The functional group-free acrylic polymer may be contained in any amount. The acrylic polymer content of the dermal adhesive composition is preferably 1 to 20 mass %, more preferably 5 to 18 mass %, still more preferably 7.5 to 15 mass %. The use of the functional group-free acrylic polymer in an amount described above in combination with the aforementioned reactive diluent leads to an effective reduction in viscosity of the dermal adhesive composition and an effective improvement in cohesiveness of the adhesive.

[Softener]

Examples of the softener (plasticizer) usable in the dermal adhesive composition include oils, such as mineral oil, vegetable oil, animal oil, and synthetic oil. Examples of the mineral oil include paraffinic and naphthenic oil. Examples of the vegetable oil include olive oil, castor oil, and palm oil. Examples of the animal oil include lanolin, turtle oil, and beeswax. Examples of the synthetic oil include silicone oil and ester oil.

[Tackifier]

Examples of the tackifier usable in the dermal adhesive composition include rosin derivatives, terpene resins, and coumarone-indene resins.

In the case of incorporation of a tackifier into the dermal adhesive composition, the tackifier content of the composition is preferably 1 to 20 mass %, more preferably 5 to 15 mass %. Incorporation of the tackifier in an amount within the above range can provide the dermal adhesive with an appropriate adhesive force.

[Filler]

Examples of the filler usable in the dermal adhesive composition include silica, alumina, and talc. Such a filler is incorporated into the dermal adhesive composition for, for example, imparting thixotropy to the composition.

[pH Adjuster]

Examples of the pH adjuster usable in the dermal adhesive composition include anhydrous citric acid, alkali metal hydroxides, and organic acid buffers.

[Pharmaceutically Active Ingredient]

The dermal adhesive composition of the present embodiment may contain any pharmaceutically active ingredient that does not impair the advantageous effects of the present technique. Examples of the pharmaceutically active ingredient include drugs, such as biological activators, antibacterial agents, anti-inflammatory analgesic agents, steroids, anesthetics, antifungal agents, bronchodilators, antitussives, coronary vasodilators, antihypertensive agents, hypotensive diuretics, antihistamine agent, hypnotics and sedatives, tranquilizers, vitamins, sex hormones, antidepressants, ameliorants of cerebral circulation, antiemetics, and antitumor agents. Such a drug systemically or locally exerts its effects through transdermal absorption, or locally exerts its effects at a portion to which the dermal adhesive is applied.

The dermal adhesive composition used for formation of the dermal adhesive of the present embodiment is prepared to have a dynamic viscosity at 115° C. and 1 Hz of preferably 500 Pa·s or less, more preferably 300 Pa·s or less, still more preferably 250 Pa·s or less.

The dermal adhesive composition having a dynamic viscosity within the above range is readily applied to an adherend. For example, the composition is suitable for coating with a hot-melt processor.

<Method for Producing Dermal Adhesive>

Now will be described a method for producing the dermal adhesive of the present embodiment.

The method for producing the dermal adhesive of the present embodiment involves step A) applying a radiation-curable resin or a dermal adhesive composition containing the radiation-curable resin to an adherend (hereinafter step A will be referred to as "application step"), and step B) irradiating the dermal adhesive composition with radiation rays (hereinafter step B will be referred to as "irradiation step"). The application step involves application of the dermal adhesive composition so as to form a porous membranous dermal adhesive.

The dermal adhesive composition may be applied to any adherend; for example, a base sheet used for a patch described below or a release sheet.

Examples of the application step of forming a porous membranous dermal adhesive include a printing process using a printing plate with a porous pattern, a transfer process using a transfer material with a porous pattern, a blowing process of application of fibers of the dermal adhesive composition, or a dispensing process. Among these processes, the blowing process is preferred in view of easy formation of a porous membranous dermal adhesive composed of fibrous or particulate resins containing a radiation-curable resin and having voids between the fibrous or particulate resins. More preferred is a melt blowing process involving discharge of a heated dermal adhesive composition in a fibrous and/or particulate form and application of the discharged dermal adhesive composition. The melt blowing process is suitable for use if the radiation-curable resin contained in the dermal adhesive composition is a hot-melt ultraviolet ray-curable resin.

In specific, the melt blowing process is preferably a curtain spray coating process involving discharge of a fibrous or particulate dermal adhesive composition, a spiral spraying process involving discharge of spiral fibers of the composition, or a bead coating process involving linear discharge of fibers of the composition. The dermal adhesive composition is applied through the melt blowing process at a temperature of preferably 60 to 150° C., more preferably 70° C. to 140° C., still more preferably 80° C. to 130° C. The melt blowing process may be carried out with a commercially available hot-melt applicator.

Blowing of hot air to the discharged resin (dermal adhesive composition) during application of the resin by the melt blowing process is preferred in view of formation of appropriate fibrous or particulate resins and preparation of a uniform non-woven pattern at a constant productivity. The hot air may have any temperature. The hot air temperature is preferably 100 to 300° C., more preferably 150° C. to 270° C.

In the application step, the dermal adhesive composition may be applied to the adherend in any amount per unit area of the adherend (g/m$^2$), so long as a porous membranous dermal adhesive is formed. The amount of application is preferably 5 to 500 g/m$^2$, more preferably 10 to 300 g/m$^2$, still more preferably 20 to 200 g/m$^2$, in view of formation of a porous membranous dermal adhesive exhibiting high breathability and adhesion. An amount of the applied composition within the above preferred range leads to maintenance of the porous membranous structure of the dermal adhesive even after collapse of fibrous resins or particulate resins.

The dose of the radiation rays in the irradiation step may be at any level so long as curing of the radiation-curable resin is achieved.

If the radiation-curable resin is, for example, an ultraviolet ray-curing resin having a thickness of 100 μm, the cumulative amount of ultraviolet rays (wavelength: 200 to 400 nm) may be appropriately adjusted to 10 to 1,000 mJ/cm$^2$. In this case, the cumulative amount of ultraviolet rays is preferably 100 to 400 mJ/cm$^2$. The amount of ultraviolet rays is determined with UV POWER PUCK II (trade name) manufactured by Electronic Instrumentation and Technology Inc.

If the radiation-curable resin is an electron beam-curable resin, the cumulative amount of electron beams may be appropriately adjusted to 1 to 100 kGy, for example.

During the production of the dermal adhesive of the present embodiment, the application step and the irradiation step are preferably preceded by a step of mixing the dermal adhesive composition. The mixing step may be carried out with any device, such as an agitator, a kneader, or a roller. The mixing step may be carried out at any temperature for any period of time. The mixing temperature and time are appropriately determined depending on the components contained in the dermal adhesive composition.

If the dermal adhesive composition contains a hot-melt ultraviolet ray-curable resin (i.e., a preferred radiation-curable resin), the mixing step is preferably carried out under heating of the dermal adhesive composition at 50 to 180° C. in view of easy mixing of the composition. The temperature of the mixing step is preferably 70 to 160° C., more preferably 80 to 140° C., still more preferably 80° C. to 100° C., in view of easy mixing of the dermal adhesive composition. Although the dermal adhesive composition can be well mixed at a low temperature because of shearing action, a load is applied to the mixer at a very low temperature. Thus, the aforementioned temperature range is preferred in view of productivity. In this case, the hot-melt ultraviolet ray-curable resin is heated to a temperature of preferably 50 to 180° C., more preferably 70 to 160° C., still more preferably 80 to 140° C., before incorporation of components other than the hot-melt ultraviolet ray-curable resin. Heating of the hot-melt ultraviolet ray-curable resin to such a temperature facilitates mixing of the resin with the other components.

As detailed above, the dermal adhesive of the present embodiment has a porous membranous structure formed through irradiation of the radiation-curable resin with radiation rays. Thus, the dermal adhesive exhibits high breathability and can reduce stuffiness that causes rash or itch.

In the case of a dermal adhesive prepared from a radiation-curable resin, the thickness of the dermal adhesive needs to be reduced so as not to cause insufficient curing of the radiation-curable resin. The present inventors have found that a reduction in thickness of the dermal adhesive leads to a reduction in amount of a water-absorbable hydrophilic polymer contained in the dermal adhesive, resulting in unsatisfactory water absorbance of the adhesive. The present inventors have also found that a porous membranous dermal adhesive formed through irradiation of a radiation-curable resin with radiation rays can reduce stuffiness that causes rash or itch.

The dermal adhesive of the present embodiment contains a radiation-curable resin as a main component. Thus, the dermal adhesive can be readily formed and applied to a base sheet without a solvent, and the dermal adhesive exhibits safety to the skin.

The porous membranous dermal adhesive is formed through combination of fibrous resins containing the radiation-curable resin and has voids defined between the fibrous resins. Accordingly, the dermal adhesive exhibits high breathability and favorable texture to the skin. Thus, the dermal adhesive provides the user with comfort and can be applied to the skin for a long period of time.

The porous membranous dermal adhesive has a surface area larger than that of a non-porous or solid adhesive layer, and thus exhibits higher water absorbance.

The dermal adhesive of the present embodiment can be used in a patch as detailed below.

<Patch>

The patch according to an embodiment of the present technique includes a base sheet and a dermal adhesive disposed on the base sheet (hereinafter the adhesive may be referred to as "adhesive layer"). The adhesive layer corresponds to the dermal adhesive according to the aforementioned embodiment of the present technique.

The patch of the present embodiment is suitable for use as an adhesive in, for example, a wound dressing applied to a living body, a surgical tape, a tape for fixation of a catheter or an infusion tube, a patch for an ostomy appliance, a poultice, a patch for fixation of an electrocardiographic electrode or a magnetic therapeutic device, or a patch for the purpose of skin care or beauty care. The dermal adhesive of the aforementioned embodiment, which is in the form of a porous membrane, exhibits high breathability, and thus is suitable for use in a wound dressing or a patch for an ostomy appliance.

The patch of the present embodiment used as a wound dressing can effectively absorb moisture (e.g., sweat or exudate from a wound), and thus can provide a wet environment suitable for wound healing and contribute to an improvement in wound healing. The patch of the present embodiment used for an ostomy appliance can effectively absorb moisture from sweat or excrement and provide the skin with a comfort and less irritating feeling.

The patch may include any base sheet that can support the adhesive layer. The base sheet may be in the form of a planar structure, such as a film, a sheet, or a plate (hereinafter collectively referred to as "sheet"), or in the form of a three-dimensional structure composed of, for example, a plastic or rubber material.

The patch may be in the form of a dermal adhesive sheet including a base sheet. The dermal adhesive sheet may have any shape; for example, a polygonal shape, such as a triangular, rectangular, or rhombic shape, a circular shape, an elliptical shape, or any combination of these shapes. The dermal adhesive sheet may be in the form of, for example, a tape extending in a specific direction or a roll. The dermal adhesive sheet may have a three-dimensional structure that conforms to the shape of a site to which the sheet is applied, or may be provided with cutouts or slits.

The base sheet may have any thickness. The thin base sheet allows radiation rays to be applied not only to the dermal adhesive layer, but also from behind the base sheet, resulting in an improvement in productivity. From this viewpoint, the thickness of the base sheet is preferably 1 to 200 μm, more preferably 5 to 100 μm, still more preferably 10 to 50 μm. A reduction in thickness of the base sheet leads to an improvement in conformation of the sheet to the skin and allows the sheet to be irradiated with radiation rays for curing of the radiation-curable resin, resulting in an improvement in productivity.

Examples of the base sheet include non-woven fabrics, knitted fabrics, woven fabrics, plastic sheets, rubber sheets, foam sheets, and paper sheets. Among these base sheets, preferred are plastic sheets in view of, for example, softness, elasticity, appropriate moisture permeation, and bacterial barrier properties.

Examples of the material of plastic sheets include polyurethanes; polyesters, such as polyethylene terephthalate) and poly(butylene terephthalate); polyamides, such as nylon 6 and nylon 66; polyolefins, such as polyethylene and polypropylene; olefinic copolymers, such as ethylene-vinyl acetate (EVA) copolymers and ethylene-alkyl (meth)acrylate copolymers; and silicones, such as polydimethylsiloxane.

Among the aforementioned materials of plastic sheets, preferred are polyethylenes, polyurethanes, polyesters, and polyamides in the present embodiment, in view of favorable moisture permeation and less inhibition of insensible perspiration. These materials may be used alone or in combination. The plastic sheet may have a layered structure composed of two or more materials.

The dermal adhesive sheet preferably has breathability. The dermal adhesive sheet exhibits a breathability (air permeability) of preferably 1.5 seconds or less, more preferably 1.3 seconds or less, still more preferably 1.0 second or less, as measured in accordance with method B (Gurley method) of JIS L1096. The dermal adhesive sheet having an air permeability within the above range exhibits high breathability and can readily reduce stuffiness that causes rash or itch.

The dermal adhesive sheet preferably has moisture permeability. As used herein, the term "moisture permeability" refers to the ability of the dermal adhesive sheet to discharge moisture generated from the body to the outside of the sheet during the use of the sheet. The moisture permeability is determined in accordance with JIS K6404 and JIS L1099 A-2 "water method." The lower limit of the moisture permeability is preferably 100 $g/m^2 \cdot 24$ hr, more preferably 150 $g/m^2 \cdot 24$ hr, still more preferably 200 $g/m^2 \cdot 24$ hr. The upper limit of the moisture permeability is preferably 10,000 $g/m^2 \cdot 24$ hr, more preferably 3,000 $g/m^2 \cdot 24$ hr, still more preferably 2,000 $g/m^2 \cdot 24$ hr. The dermal adhesive sheet having a moisture permeability within the above range can readily reduce stuffiness that causes rash or itch.

The adhesive sheet having an air permeability and a moisture permeability within the aforementioned preferred ranges exhibits high breathability and water vapor permeability and can readily reduce stuffiness that causes rash or itch.

The patch of the present embodiment, which includes the base sheet and the adhesive layer, may be provided with a release sheet on the adhesive layer. The release sheet protects the adhesive layer from contamination and facilitates handling of the dermal adhesive sheet.

The release sheet may be treated with a silicone resin or a fluororesin or may be embossed.

The present technique includes the following aspects [1] to [13]:

Aspect [1]: A dermal adhesive in the form of a porous membrane formed through irradiation of a radiation-curable resin with radiation rays.

Aspect [2]: The dermal adhesive according to Aspect [1], having a porosity of 5 to 90%.

Aspect [3]: The dermal adhesive according to Aspect [1] or [2], wherein fibrous resins and/or particulate resins containing the radiation-curable resin are aggregated to define voids between the fibrous resins and/or the particulate resins, to be prepared in the form of the porous membrane.

Aspect [4]: The dermal adhesive according to any one of Aspects [1] to [3], formed through discharge of a dermal adhesive composition comprising the radiation-curable resin in a fibrous and/or particulate form, and irradiation of the discharged dermal adhesive composition with the radiation rays.

Aspect [5]: The dermal adhesive according to any one of Aspects [1] to [4], further comprising a hydrophilic polymer dispersed in the radiation-curable resin.

Aspect [6]: The dermal adhesive according to Aspect [5], wherein the amount of the radiation-curable resin is 35 to 95 mass %, and the amount of the hydrophilic polymer is 1 to 30 mass %.

Aspect [7]: The dermal adhesive according to Aspect [6], further comprising a reactive diluent that reacts with the radiation-curable resin, and a functional group-free acrylic polymer, wherein the radiation-curable resin is an ultraviolet ray-curable resin, the amount of the ultraviolet ray-curable resin is 35 to 95 mass %, the amount of the hydrophilic polymer is 1 to 30 mass %, the amount of the reactive diluent is 1 to 20 mass %, and the amount of the functional group-free acrylic polymer is 1 to 20 mass %.

Aspect [8]: A patch comprising a base sheet and the dermal adhesive according to any one of Aspects [1] to [7], the dermal adhesive being disposed on the base sheet.

Aspect [9]: A method for producing a porous membranous dermal adhesive, the method comprising:

A) applying a dermal adhesive composition containing a radiation-curable resin to an adherend so as to form a porous membranous dermal adhesive, and B) irradiating the dermal adhesive composition with radiation rays.

Aspect [10]: The method according to Aspect [9], wherein step A) comprises discharging, in a melt blowing process, the dermal adhesive composition in a fibrous and/or particulate form while heating the dermal adhesive composition by a melt blowing process.

Aspect [11]: The method according to Aspect [9] or [10], wherein step A) comprises discharging the dermal adhesive composition in the form of fibers and/or particles, and applying the dermal adhesive composition to the adherend while blowing hot air of 100 to 300° C. to the dermal adhesive composition.

Aspect [12]: The method according to any one of Aspects [9] to [11], wherein the dermal adhesive composition contains 35 to 95 mass % the radiation-curable resin and 1 to 30 mass % a hydrophilic polymer.

Aspect [13]: The method according to any one of Aspects [9] to [12], wherein the radiation-curable resin is an ultraviolet ray-curable resin, and the dermal adhesive composition contains 35 to 95 mass % the radiation-curable resin, 1 to 30 mass % the hydrophilic polymer, 1 to 20 mass % a reactive diluent that reacts with the radiation-curable resin, and 1 to 20 mass % a functional group-free acrylic polymer.

EXAMPLES

The present technique will now be described by way of experimental examples. The following examples are mere typical experimental examples of the present technique and should not be construed to limit the present technique. Unless otherwise specified, the "mass %" in the following description is relative to the total mass of an adhesive composition.

Experimental Example 1

For formation of a dermal adhesive, a dermal adhesive composition was prepared through mixing of components described below.

An ultraviolet ray-curable resin (trade name of "acResin A260UV," a polymer having a structural unit derived from butyl acrylate, manufactured by BASF) (75.5 mass %) was used as a radiation-curable resin. The resin was heated to 120° C.

The resin was mixed with a reactive diluent; specifically, PO-modified trimethylolpropane triacrylate (trade name of "TMP-3P," manufactured by DKS Co., Ltd., viscosity at 25° C.: 60 mPa·s) (2.5 mass %), and then mixed with a functional group-free acrylic polymer (trade name of "ARUFON (registered trademark) UP-1000," manufactured by TOAGOSEI CO., LTD., liquid form at 25° C., Mw: 3,000, viscosity at 25° C.: 1,000 mPa·s, Tg: −77° C., solid content: 98% or more) (10.0 mass %). The resultant mixture was further mixed with sodium carboxymethyl cellulose (hereinafter referred to as "CMC.Na," manufactured by Nippon Paper Industries Co., Ltd.) serving as a hydrophilic polymer (10.0 mass %), silica (manufactured by Tosoh Silica Corporation) serving as a filler (1.0 mass %), and ceramide serving as a biological activator (1.0 mass %). The resultant mixture was agitated to prepare a dermal adhesive composition used in Experimental Example 1.

The dermal adhesive composition was discharged, in a melt blowing process, in the form of fibers and/or particles under heating, and then applied to an adherend.

In detail, the dermal adhesive composition was applied (amount: 50 g/m$^2$, thickness: 100 μm) to a PET film having a thickness of 25 μm (Lumilar (registered trademark)-25-S10, manufactured by Toray Industries, Inc.) with a curtain spray coater under the following conditions: tank temperature: 130° C., hose temperature: 140° C., extruder temperature: 140° C., head temperature: 150° C., hot air temperature: 230° C., and air pressure: 0.2 MPa. During this application step with the curtain spray coater, the heated dermal adhesive composition was discharged in the form of fibers and particles.

The dermal adhesive composition applied to the PET film was irradiated with ultraviolet rays (cumulative amount of light: about 100 mJ/cm$^2$) by use of an ultraviolet irradiator, to form a dermal adhesive of Experimental Example 1 on the PET film. A dermal adhesive sheet of Experimental Example 1 was thereby prepared. The dermal adhesive of Experimental Example 1 was in the form of a porous membrane prepared through combination of fibrous resins and particulate resins of the dermal adhesive composition (containing the ultraviolet ray-curable resin) and having voids between the fibrous resins and/or the particulate resins (see FIG. 3).

The surface of the dermal adhesive of Experimental Example 1 was photographed with an optical microscope (Digital Microscope VH-8000 (trade name), manufactured by KEYENCE CORPORATION). FIG. 3 is a photographic image (substitute for drawing) of the surface. The image was analyzed with image analysis software (Winroof (trade name), manufactured by Mitsubishi Corporation) to determine the porosity of the dermal adhesive of Experimental Example 1, the fiber diameter of fibrous resins, and the particle size of particulate resins. The porosity was determined through calculation of the ratio of the areas of pores (black regions in FIG. 3) to the total area of the image by the "cell extraction" mode (i.e., image analysis mode) of the image analysis software. For determination of the fiber diameter of the fibrous resin, three measuring points were randomly selected in fibrous resins in the optical microscopic image (FIG. 3), and the fiber diameter (fiber thicknesses) was measured on the basis of the averaged diameters of the three fibrous resins of the image. The fiber length of the fibrous resin was determined on the basis of the averaged lengths as in the fiber diameter. For determination of the particle size of the particulate resin, three measuring points were randomly selected in particulate resins in the optical microscopic image (FIG. 3), and the particle size was measured at on the basis of the averaged sizes of the three particulate resins of the image.

According to the aforementioned method, the porosity was about 19.1%, the fiber diameter was about 53 μm, the fiber length was about 2.4 mm, and the particle size was about 74 μm.

(Breathability)

The breathability (air permeability) of the dermal adhesive of Experimental Example 1 was determined in accordance with method B (Gurley method) of JIS L1096. For determination of the breathability (air permeability), a dermal adhesive sheet was prepared as in the dermal adhesive sheet of Experimental Example 1, except that the "PET film" used in Experimental Example 1 was replaced with "spunbond non-woven fabric (ELEVES (registered trademark) 50403, manufactured by UNITIKA LTD.)."

(Adhesive Force)

The adhesive force (peel force) of the dermal adhesive sheet of Experimental Example 1 was determined with a tensile tester ("INSTRON 5564," manufactured by Instron) in accordance with JIS Z0237 at a tensile speed of 300 mm/min. A test piece was applied to a Bakelite plate serving as an adherend. The test piece was prepared under the same conditions and irradiation as described above. The test piece had a width of 1 inch (25.4 mm) and a length of 100 mm.

In the evaluation of the adhesive force, it was determined whether the peeling mode (i.e., how the test piece was removed from the adherend) was attributed to "interfacial peeling" (i.e., peeling at the interface between the adhesive and the adherend) or "cohesive failure" (i.e., destruction of the adhesive itself).

(Water Absorption)

The mass of the dermal adhesive sheet of Experimental Example 1 was measured before and after immersion of the sheet in saline (0.9% aqueous NaCl solution) for 24 hours. The water absorption (%) of the dermal adhesive was calculated from the following expression:

water absorption (%)={[(mass after immersion)−(mass before immersion)]/(mass before immersion)}×100

Experimental Example 2

For preparation of a dermal adhesive, a dermal adhesive composition was prepared through mixing of components described below.

An ultraviolet ray-curable resin (trade name of "acResin A260UV," a polymer having a structural unit derived from butyl acrylate, manufactured by BASF) (75.5 mass %) was used as a radiation-curable resin. The resin was heated to 120° C.

The resin was mixed with a functional group-free acrylic polymer (trade name of "ARUFON (registered trademark) UP-1000," manufactured by TOAGOSEI CO., LTD., liquid form at 25° C., Mw: 3,000, viscosity at 25° C.: 1,000 mPa·s, Tg: −77° C., solid content: 98% or more) (12.5 mass %). The resultant mixture was further mixed with CMC.Na (manufactured by Nippon Paper Industries Co., Ltd.) serving as a hydrophilic polymer (10.0 mass %), silica (manufactured by Tosoh Silica Corporation) serving as a filler (1.0 mass %), and ceramide serving as a biological activator (1.0 mass %).

The resultant mixture was agitated to prepare a dermal adhesive composition used in Experimental Example 2.

The dermal adhesive composition was discharged in a melt blowing process, in the form of fibers and/or particles under heating, and then applied to an adherend.

In detail, the dermal adhesive composition was applied (amount: 50 g/m$^2$, thickness: 100 μm) to a PET film having a thickness of 25 μm (Lumilar (registered trademark)-25-S10, manufactured by Toray Industries, Inc.) with a curtain spray coater under the following conditions: tank temperature: 90° C., hose temperature: 100° C., extruder temperature: 170° C., head temperature: 170° C., hot air temperature: 250° C., and air pressure: 0.3 MPa. During this application step with the curtain spray coater, the heated dermal adhesive composition was discharged in the form of fibers and particles.

The dermal adhesive composition applied to the PET film was irradiated with ultraviolet rays (cumulative amount of light: about 400 mJ/cm$^2$) by use of an ultraviolet irradiator, to form a dermal adhesive of Experimental Example 2 on the PET film. A dermal adhesive sheet of Experimental Example 2 was thereby prepared. The dermal adhesive of Experimental Example 2 was in the form of a porous membrane prepared through combination of fibrous resins and particulate resins of the dermal adhesive composition (containing the ultraviolet ray-curable resin) and having voids between the fibrous resins and/or the particulate resins.

The dermal adhesive of the dermal adhesive sheet of Experimental Example 2 was laminated with a PET film, and the PET film was then removed from the dermal adhesive. The surface of the dermal adhesive was then photographed with an optical microscope (Digital Microscope VH-8000 (trade name), manufactured by KEYENCE CORPORATION). FIG. 4 is a photographic image (substitute for drawing) of the surface. As illustrated in FIG. 4, the dermal adhesive of Experimental Example 2 was in the form of a porous membrane including fibrous resins and continuous segments formed through collapse of fibrous resins and particulate resins.

The air permeability, adhesive force, and water absorption of the dermal adhesive of Experimental Example 2 were determined as in Experimental Example 1. A non-woven fabric having a basis weight of 130 g/m$^2$ was used for determination of the air permeability.

The porosity, fiber length, and fiber diameter of the dermal adhesive of Experimental Example 2 were determined as in Experimental Example 1. The porosity was about 25.7%, the fiber length was about 2.7 mm, and the fiber diameter was about 60 μm.

Experimental Example 3

In Experimental Example 3, the dermal adhesive composition prepared in Experimental Example 1 was applied (amount: 300 g/m$^2$, thickness: 100 μm) to a PET film having a thickness of 25 μm (Lumilar (registered trademark)-25-S10, manufactured by Toray Industries, Inc.) with a comma coater at 120° C. The dermal adhesive composition applied to the PET film was irradiated with ultraviolet rays (cumulative amount of light: about 200 mJ/cm$^2$) by use of an ultraviolet irradiator, to form a dermal adhesive of Experimental Example 3 on the PET film. A dermal adhesive sheet of Experimental Example 3 was thereby prepared. The dermal adhesive of Experimental Example 3 was in the form of a substantially even, solid layer disposed on the PET film.

The air permeability, adhesive force, and water absorption of the dermal adhesive of Experimental Example 3 were determined as in Experimental Example 1.

Table 1 shows the components of the dermal adhesive compositions used in the aforementioned Experimental Examples, and the breathability, adhesive force, and water absorption of the dermal adhesives.

[Table 1]

| | | Experimental Example 1 | Experimental Example 2 | Experimental Example 3 |
|---|---|---|---|---|
| Composition (mass %) | Ultraviolet ray-curable resin | 75.5 | 75.5 | 75.5 |
| | PO-modified trimethylolpropane triacrylate | 2.5 | — | 2.5 |
| | Functional group-free acrylic polymer | 10.0 | 12.5 | 10.0 |
| | Silica | 1.0 | 1.0 | 1.0 |
| | CMC · Na | 10.0 | 10.0 | 10.0 |
| | Ceramide | 1.0 | 1.0 | 1.0 |
| Form of dermal adhesive | | Porous membrane | Porous membrane | Solid layer |
| Air permeability (second) | | <1 | <1 | No air permeation |
| Adhesive force (N/25 mm) | | 5.2 | 6.4 | 7.7 |
| Peeling mode during evaluation of adhesive force | | Interfacial peeling | Interfacial peeling | Interfacial peeling |
| Water absorption (%) | | 106 | 128 | 127 |

As shown in Table 1, the dermal adhesives of Experimental Examples 1 and 2 exhibited appropriate adhesive force and water absorption, and breathability (air permeability) higher than that of the dermal adhesive of Experimental Example 3 in the form of a solid layer. These advantageous effects are attributed to the porous membranous form of the dermal adhesives of Experimental Examples 1 and 2. Each of the dermal adhesives of Experimental Examples 1 and 2 was prepared through application of the dermal adhesive composition in a fibrous and particulate form, and was in the form of a porous membrane prepared through combination of fibrous resins and particulate resins containing the ultraviolet ray-curable resin and having voids defined between the fibrous resins and between the fibrous resins and the particulate resins. This porous membranous form achieved appropriate adhesive force and high breathability and water absorption.

REFERENCE SIGNS LIST 1, 11: dermal adhesive
2, 21: fibrous resin
3: particulate resin
4, 41: void
5: continuous segment

The invention claimed is:
1. A dermal adhesive in the form of a porous membrane formed through irradiation of a radiation-curable resin with radiation rays, comprising:
   fibrous resins containing the radiation-curable resin;
   particulate resins containing the radiation-curable resin;
   a hydrophilic polymer dispersed in the radiation-curable resin;
   a reactive diluent that reacts with the radiation-curable resin; and
   a functional group-free acrylic polymer, wherein the dermal adhesive has a porosity of 5 to 90% and voids between the fibrous resins and particulate resins, wherein the radiation-curable resin is an ultraviolet ray-curable resin, wherein in the dermal adhesive an amount of the radiation-curable resin is 35 to 95 mass %, an amount of the hydrophilic polymer is 1 to 30 mass %, an amount of the reactive diluent is 1 to 20 mass %, and an amount of the functional group-free acrylic polymer is 1 to 20 mass %, and wherein the fiber diameter of each of the fibrous resins is from 1 to 1000 µm, and the length of each of the fibrous resins is from 0.1 to 10 mm, and wherein the particle size of each of the particulate resins is from 1 to 1000 µm.

2. A patch comprising:
a base sheet; and
the dermal adhesive according to claim 1, the dermal adhesive being disposed on the base sheet.

3. A dermal adhesive in the form of a porous membrane formed through irradiation of a radiation-curable resin with radiation rays, comprising:
fibrous resins containing the radiation-curable resin;
particulate resins containing the radiation-curable resin;
a hydrophilic polymer dispersed in the radiation-curable resin; and
a functional group-free acrylic polymer,
wherein the dermal adhesive has a porosity of 5 to 90% and voids between the fibrous resins and the particulate resins,
wherein the radiation-curable resin is an ultraviolet ray-curable resin,
wherein in the dermal adhesive an amount of radiation-curable resin is 35 to 95 mass %, an amount of the hydrophilic polymer is 1 to 30 mass %, and an amount of the functional group-free acrylic polymer is 1 to 20 mass %, and
wherein the fiber diameter of each of the fibrous resins is from 1 to 1000 µm, and the length of each of the fibrous resins is from 0.1 to 10 mm, and
wherein the particle size of each of the particulate resins is from 1 to 1000 µm.

4. A patch comprising:
a base sheet; and
the dermal adhesive according to claim 3, the dermal adhesive being disposed on the base sheet.

5. A dermal adhesive in the form of a porous membrane formed through irradiation of a radiation-curable resin with radiation rays, consisting of:
fibrous resins containing the radiation-curable resin;
particulate resins containing the radiation-curable resin;
a hydrophilic polymer dispersed in the radiation-curable resin; and
a functional group-free acrylic polymer,
wherein the dermal adhesive has a porosity of 5 to 90% and voids between the fibrous resins and the particulate resins,
wherein the radiation-curable resin is an ultraviolet ray-curable resin,
wherein in the dermal adhesive an amount of the radiation-curable resin is 35 to 95 mass %, an amount of the hydrophilic polymer is 1 to 30 mass %, and an amount of the functional group-free acrylic polymer is 1 to 20 mass %, and
wherein the fiber diameter of each of the fibrous resins is from 1 to 1000 µm, the length of each of the fibrous resins is from 0.1 to 10 mm, and
wherein the particle size of each of the particulate resins is from 1 to 1000 µm.

6. A patch comprising:
a base sheet; and
the dermal adhesive according to claim 5, the dermal adhesive being disposed on the base sheet.

7. The dermal adhesive of claim 1 wherein in the dermal adhesive an amount of the fibrous resins is greater than an amount of the particulate resins.

8. The dermal adhesive of claim 3 wherein in the dermal adhesive an amount of the fibrous resins is greater than an amount of the particulate resins.

9. The dermal adhesive of claim 5 wherein in the dermal adhesive an amount of the fibrous resins is greater than an amount of the particulate resins.

10. The dermal adhesive of claim 7 wherein the fibrous resins form a nonwoven fabric structure in the dermal adhesive.

11. The dermal adhesive of claim 8 wherein the fibrous resins form a nonwoven fabric structure in the dermal adhesive.

12. The dermal adhesive of claim 9 wherein the fibrous resins form a nonwoven fabric structure in the dermal adhesive.

* * * * *